(12) United States Patent
Moriura et al.

(10) Patent No.: US 11,932,263 B2
(45) Date of Patent: Mar. 19, 2024

(54) TRAVEL SICKNESS ESTIMATION SYSTEM, MOVING VEHICLE, TRAVEL SICKNESS ESTIMATION METHOD, AND TRAVEL SICKNESS ESTIMATION PROGRAM

(71) Applicant: PANASONIC INTELLECTUAL PROPERTY MANAGEMENT CO., LTD., Osaka (JP)

(72) Inventors: Yuta Moriura, Osaka (JP); Yoshitaka Nakamura, Osaka (JP); Yasufumi Kawai, Osaka (JP); Hiroyuki Handa, Osaka (JP); Yohei Morishita, Kanagawa (JP); Toru Okino, Osaka (JP); Hiroyuki Hagino, Osaka (JP); Toru Sakuragawa, Osaka (JP); Satoshi Morishita, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 842 days.

(21) Appl. No.: 16/980,222

(22) PCT Filed: Mar. 13, 2019

(86) PCT No.: PCT/JP2019/010203
§ 371 (c)(1),
(2) Date: Sep. 11, 2020

(87) PCT Pub. No.: WO2019/177002
PCT Pub. Date: Sep. 19, 2019

(65) Prior Publication Data
US 2021/0031789 A1 Feb. 4, 2021

(30) Foreign Application Priority Data
Mar. 14, 2018 (JP) ................ 2018-047188

(51) Int. Cl.
*B60W 50/00* (2006.01)
*A61B 5/11* (2006.01)
(Continued)

(52) U.S. Cl.
CPC ....... *B60W 50/0098* (2013.01); *A61B 5/1114* (2013.01); *A61B 5/1116* (2013.01);
(Continued)

(58) Field of Classification Search
CPC ............. B60W 50/0098; B60W 50/14; B60W 2540/22; B60W 2540/221;
(Continued)

(56) References Cited

U.S. PATENT DOCUMENTS

2007/0192038 A1   8/2007  Kameyama
2017/0150930 A1*  6/2017  Shikii ................. A61B 5/165

FOREIGN PATENT DOCUMENTS

JP   2004-299569 A   10/2004
JP   2005-326962 A   11/2005
(Continued)

OTHER PUBLICATIONS

International Search Report and Written Opinion issued in International Patent Application No. PCT/JP2019/010203, dated Jun. 18, 2019; with partial English translation.
(Continued)

*Primary Examiner* — Frederick M Brushaber
(74) *Attorney, Agent, or Firm* — Rimon P.C.

(57) ABSTRACT

A travel sickness estimation system includes an estimation unit and an output unit. The estimation unit is configured to perform estimation processing of estimating, based on person information indicating conditions of a person who is on board a moving vehicle, whether or not the person is in circumstances that would cause travel sickness for him or (Continued)

her. The output unit is configured to output a result of the estimation processing performed by the estimation unit.

18 Claims, 6 Drawing Sheets

(51) Int. Cl.
*A61B 5/16* (2006.01)
*A61M 21/02* (2006.01)
*B60H 1/00* (2006.01)
*B60H 3/00* (2006.01)
*B60N 2/02* (2006.01)
*B60W 50/14* (2020.01)
*A61B 5/024* (2006.01)
*A61M 21/00* (2006.01)

(52) U.S. Cl.
CPC ............ *A61B 5/1121* (2013.01); *A61B 5/165* (2013.01); *A61M 21/02* (2013.01); *B60H 1/00742* (2013.01); *B60H 3/0007* (2013.01); *B60H 3/0085* (2013.01); *B60N 2/02* (2013.01); *B60W 50/14* (2013.01); *A61B 5/02444* (2013.01); *A61B 2562/0247* (2013.01); *A61M 2021/0016* (2013.01); *A61M 2021/0022* (2013.01); *A61M 2021/0066* (2013.01); *A61M 2205/3303* (2013.01); *A61M 2205/3553* (2013.01); *A61M 2205/3584* (2013.01); *B60W 2540/22* (2013.01); *B60W 2540/221* (2020.02); *B60W 2540/223* (2020.02); *B60W 2756/10* (2020.02)

(58) Field of Classification Search
CPC ....... B60W 2540/223; B60W 2756/10; B60W 40/08; A61B 5/1114; A61B 5/1116; A61B 5/1121; A61B 5/165; A61B 5/02444; A61B 2562/0247; A61B 5/0077; A61B 5/02405; A61B 5/0507; A61B 5/0816; A61B 5/1071; A61B 10/00; A61M 21/02; A61M 2021/0016; A61M 2021/0022; A61M 2021/0066; A61M 2205/3303; A61M 2205/3553; A61M 2205/3584; A61M 2021/0027; A61M 2205/332; A61M 2205/3358; A61M 2205/505; A61M 2230/06; A61M 2230/42; A61M 2230/50; A61M 2230/62; B60H 1/00742; B60H 3/0007; B60H 3/0085; B60N 2/02; B60N 2/04; G16H 50/30; G16H 50/20; G16H 20/30; G16H 40/63; A63F 13/211; G08G 1/16

See application file for complete search history.

(56) References Cited

FOREIGN PATENT DOCUMENTS

| | | | |
|---|---|---|---|
| JP | 2006-027347 A | 2/2006 | |
| JP | 2006-027510 A | 2/2006 | |
| JP | 2006-034576 A | 2/2006 | |
| JP | 2007-212421 A | 8/2007 | |
| JP | 2007-236644 A | 9/2007 | |
| JP | 2012-059274 A | 3/2012 | |
| JP | 2012-131269 A | 7/2012 | |
| JP | 2015-182564 A | 10/2015 | |
| JP | 2017-099846 A | 6/2017 | |
| JP | 2017-132364 A | 8/2017 | |
| JP | 2017-223591 A | 12/2017 | |
| JP | 2018-032339 A | 3/2018 | |
| WO | WO-2008033540 A2 * | 3/2008 | ............ A61M 21/02 |
| WO | WO-2016197068 A1 * | 12/2016 | ........... A61B 5/4023 |

OTHER PUBLICATIONS

Extended Search Report dated Mar. 24, 2021, issued in corresponding European Patent Application No. 19768332.9.

* cited by examiner

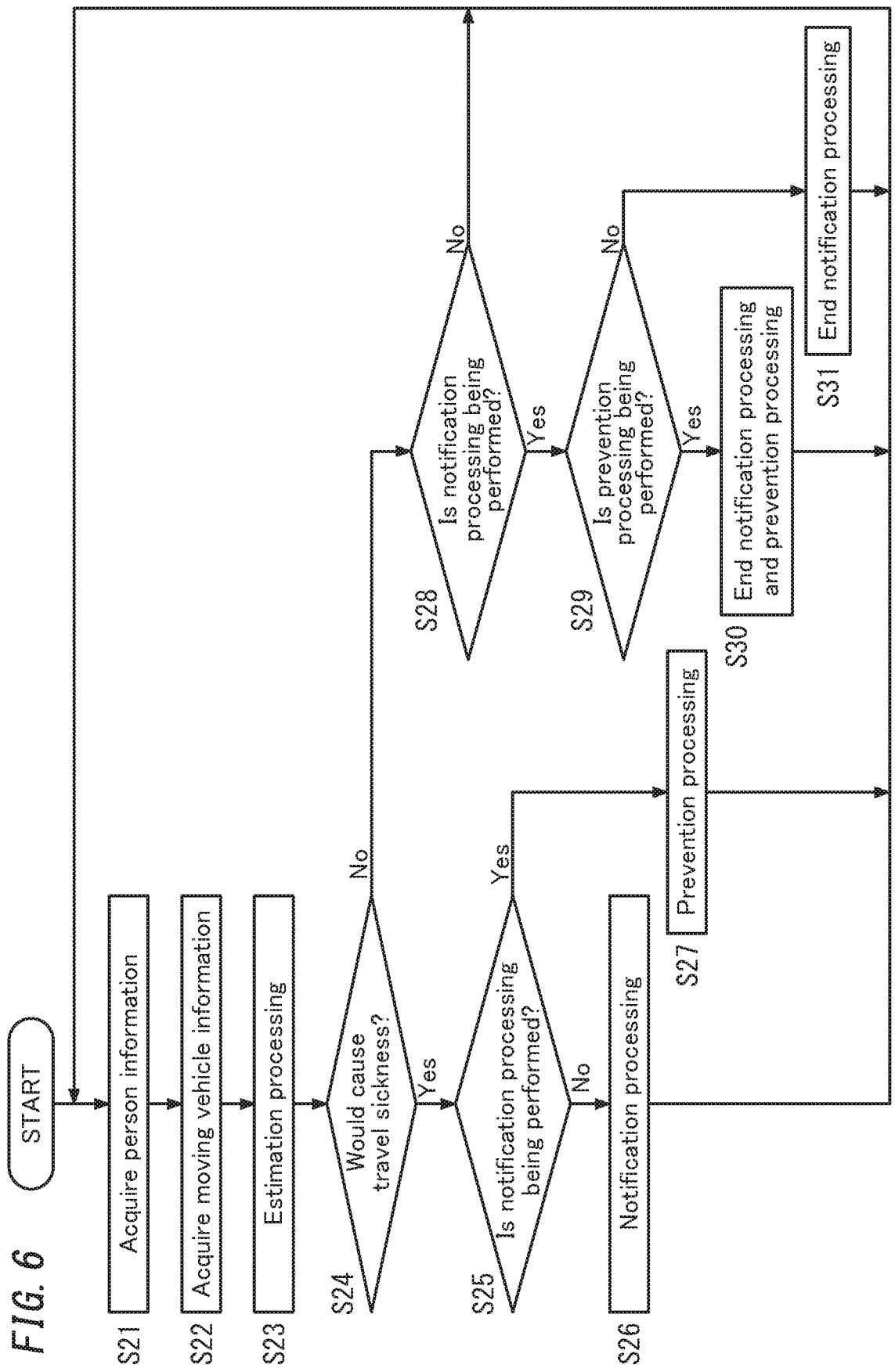

TRAVEL SICKNESS ESTIMATION SYSTEM, MOVING VEHICLE, TRAVEL SICKNESS ESTIMATION METHOD, AND TRAVEL SICKNESS ESTIMATION PROGRAM

CROSS-REFERENCE OF RELATED APPLICATIONS

This application is the U.S. National Phase under 35 U.S.C. § 371 of International Patent Application No. PCT/JP2019/010203, filed on Mar. 13, 2019, which in turn claims the benefit of Japanese Application No. 2018-047188, filed on Mar. 14, 2018, the entire disclosures of which Applications are incorporated by reference herein.

TECHNICAL FIELD

The present disclosure generally relates to travel sickness estimation systems, moving vehicles, travel sickness estimation methods, and travel sickness estimation programs. More particularly, the present disclosure relates to a travel sickness estimation system, a moving vehicle, a travel sickness estimation method, and a travel sickness estimation program, all of which are configured or designed to estimate the chances of triggering the onset of travel sickness (also called "motion sickness") for a person who is on board a moving vehicle.

BACKGROUND ART

Patent Literature 1 discloses a motion sickness reduction apparatus. The motion sickness reduction apparatus of Patent Literature 1 includes a stimulating means for giving a stimulus that induces a quasi-driver head motion to a passenger in a moving vehicle. The stimulus means induces such a quasi-driver head motion to the passenger by pushing a centrifugal part of his or her body while the moving vehicle is turning and induces such a quasi-driver head motion to other passengers as well 1.

The motion sickness reduction apparatus of Patent Literature 1 induces such a quasi-driver head motion to the passenger, no matter whether or not he or she shows a sign of the onset of motion sickness (travel sickness). Therefore, if the passenger shows no sign of the onset of motion sickness (travel sickness), then the quasi-driver head motion could trigger the onset of travel sickness to the contrary.

CITATION LIST

Patent Literature

Patent Literature 1: JP 2012-131269 A

SUMMARY OF INVENTION

The problem to be solved is to provide a travel sickness estimation system, a moving vehicle, a travel sickness estimation method, and a travel sickness estimation program, all of which are configured or designed to reduce the chances of triggering the onset of travel sickness.

A travel sickness estimation system according to an aspect of the present disclosure includes: an estimation unit configured to perform estimation processing of estimating, based on person information indicating conditions of a person who is on board a moving vehicle, whether or not the person is in circumstances that would cause travel sickness for him or her; and an output unit configured to output a result of the estimation processing performed by the estimation unit.

A moving vehicle according to another aspect of the present disclosure includes: the travel sickness estimation system described above: and a body on which the travel sickness estimation system is installed.

A travel sickness estimation method according to still another aspect of the present disclosure includes: a first step of performing estimation processing of estimating, based on person information indicating conditions of a person who is on board a moving vehicle, whether or not the person is in circumstances that would cause travel sickness for him or her; and a second step of outputting a result of the estimation processing.

A travel sickness estimation program according to yet another aspect of the present disclosure is designed, when executed by one or more processors, to give a first instruction and a second instruction to the one or more processors. The first instruction is an instruction to perform estimation processing of estimating, based on person information indicating conditions of a person who is on board a moving vehicle, whether or not the person is in circumstances that would cause travel sickness for him or her. The second instruction is an instruction to output a result of the estimation processing.

BRIEF DESCRIPTION OF DRAWINGS

FIG. 6 is a flowchart showing the procedure of operation of a travel sickness estimation system according to a variation.

DESCRIPTION OF EMBODIMENTS

1. Embodiments

1.1 Overview

Figure 1:
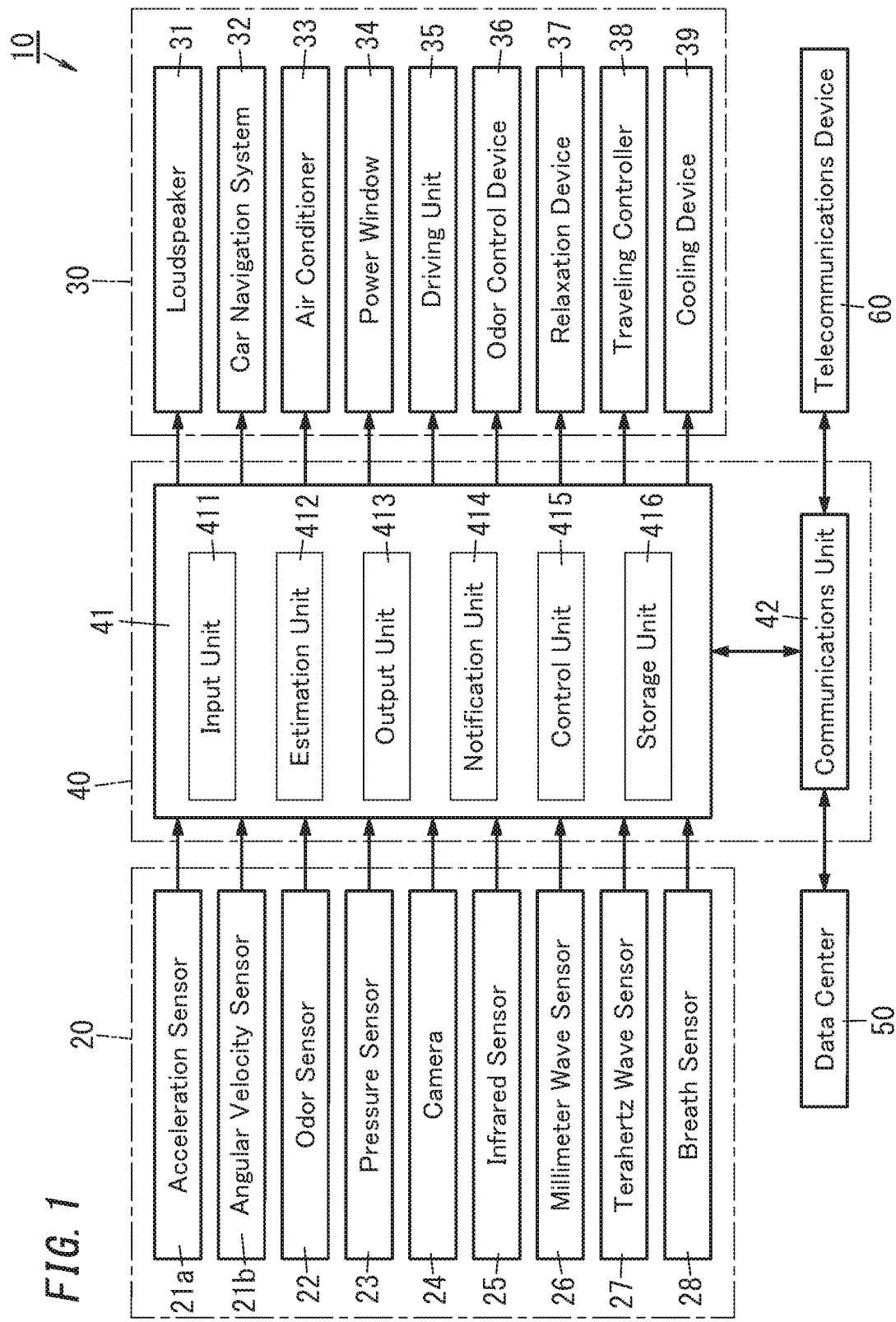
FIG. 1 is a block diagram of a travel sickness estimation system according to an exemplary embodiment.
Figure 2:
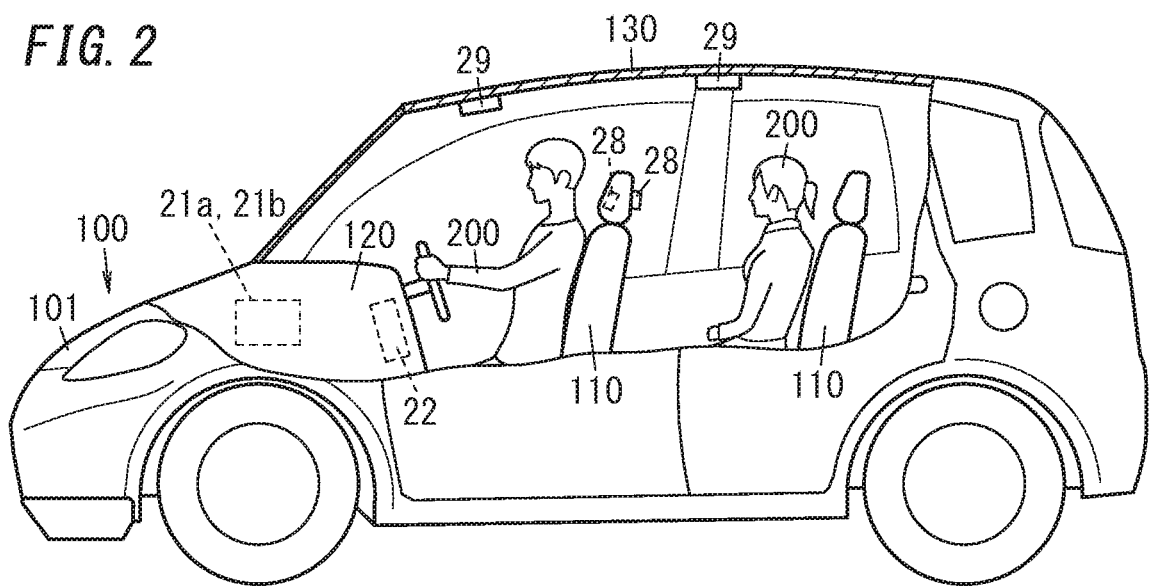
FIG. 2 illustrates a moving vehicle.

FIG. 1 illustrates a travel sickness estimation system 10 according to an exemplary embodiment. The travel sickness estimation system 10 includes an estimation unit 412 and an output unit 413. The estimation unit 412 is configured to perform estimation processing of estimating, based on person information indicating the conditions of a person 200 who is on board a moving vehicle (car 100) as shown in FIG. 2, whether or not the person 200 is in circumstances that would cause travel sickness for him or her. The output unit 413 is configured to output a result of the estimation processing performed by the estimation unit 412.

The travel sickness estimation system 10 estimates whether or not the person is in circumstances that would cause travel sickness for him or her. As used herein, estimating whether the person is in circumstances that would cause travel sickness for him or her is estimating the chances of triggering the onset of travel sickness for the person 200, not presuming whether or not the person 200 is suffering travel sickness at the current point in time. In other words, it can be said that estimating whether or not the person 200 is in circumstances that would cause travel sickness for him or her means predicting whether or not persistence of the current circumstances would cause the person 200 to have travel sickness in a predetermined amount of time (e.g., in ten minutes). That is to say, the estimation processing is estimating the chances of triggering the onset of travel sickness before the person 200 actually has travel sickness. Then, in the travel sickness estimation system 10, a result of this estimation processing is output by the output unit 413. This allows either the processing of urging the person 200 to take precautions to prevent the travel sickness or the processing of preventing the person 200 from suffering travel sickness to be performed. Thus, the travel sickness estimation system 10 reduces the onset of travel sickness.

1.2. Configuration

The travel sickness estimation system 10 will be described in further detail with reference to FIGS. 1-5. As shown in FIG. 1, the travel sickness estimation system 10 includes a sensing system 20, a device system 30, and a controller 40. FIG. 2 illustrates a car 100 as an exemplary moving vehicle to which the travel sickness estimation system 10 is applied. In the car 100, the travel sickness estimation system 10 is mounted on its body 101. The body 101 further includes seats 110, a dashboard 120, and a roof 130.

As shown in FIG. 1, the sensing system 20 includes an acceleration sensor 21a, an angular velocity sensor 21b, an odor sensor 22, a pressure sensor 23, a camera 24, an infrared sensor 25, a millimeter wave sensor 26, a terahertz wave sensor 27, and a breath sensor 28.

The acceleration sensor 21a, the angular velocity sensor 21b, and the odor sensor 22 are used to acquire moving vehicle information indicating the conditions of the moving vehicle (car 100). The moving vehicle information includes behavior information indicating the behavior of the moving vehicle (car 100) and atmosphere information indicating the atmosphere in an internal space (inside the body 101) of the moving vehicle (car 100).

The acceleration sensor 21a is installed in the body 101 as shown in FIG. 2 to measure the acceleration of the car 100. The acceleration sensor 21a is used to acquire the behavior information. The car's 100 behavior indicated by the behavior information includes the traveling direction and propulsion of the car 100. The traveling direction and propulsion of the car 100 are calculated based on the car's 100 acceleration measured by acceleration sensor 21a.

The angular velocity sensor 21b is also installed in the body 101 as shown in FIG. 2 to measure the angular velocity of the car 100. The angular velocity sensor 21b is used to acquire behavior information. The car's 100 behavior indicated by the behavior information includes a turning direction and turning speed of the car 100. The turning direction and turning speed of the car 100 are calculated based on the car's 100 angular velocity measured by the angular velocity sensor 21b.

The odor sensor 22 is used to acquire atmosphere information. Examples of the atmosphere, indicated by the atmosphere information, in the internal space of the car 100 include odors, brightness, and temperature. In this embodiment, the atmosphere information indicates an odor in the internal space of the car 100. The odor sensor 22 is a gas sensor for measuring the concentration of a gas that affects the odor. The gas that affects the odor may be, for example, a gas that tends to trigger travel sickness for the person 200. Specific examples of such gases include volatile organic compounds (such as formaldehyde, toluene, and gasoline).

The pressure sensor 23, the camera 24, the infrared sensor 25, the millimeter wave sensor 26, the terahertz wave sensor 27, and the breath sensor 28 are used to acquire person information indicating the conditions of the person 200 who is on board the moving vehicle (car 100). The person information includes posture information indicating the person's 200 posture, progress information indicating how the person's 200 biometric information has changed, and emotion information indicating (either an instantaneous value or variation of) the person's 200 emotions. Examples of the person's 200 biometric information include the breath, body temperature (particularly, nose temperature), complexion, heartbeat, respiration, and blink.

Figure 3:
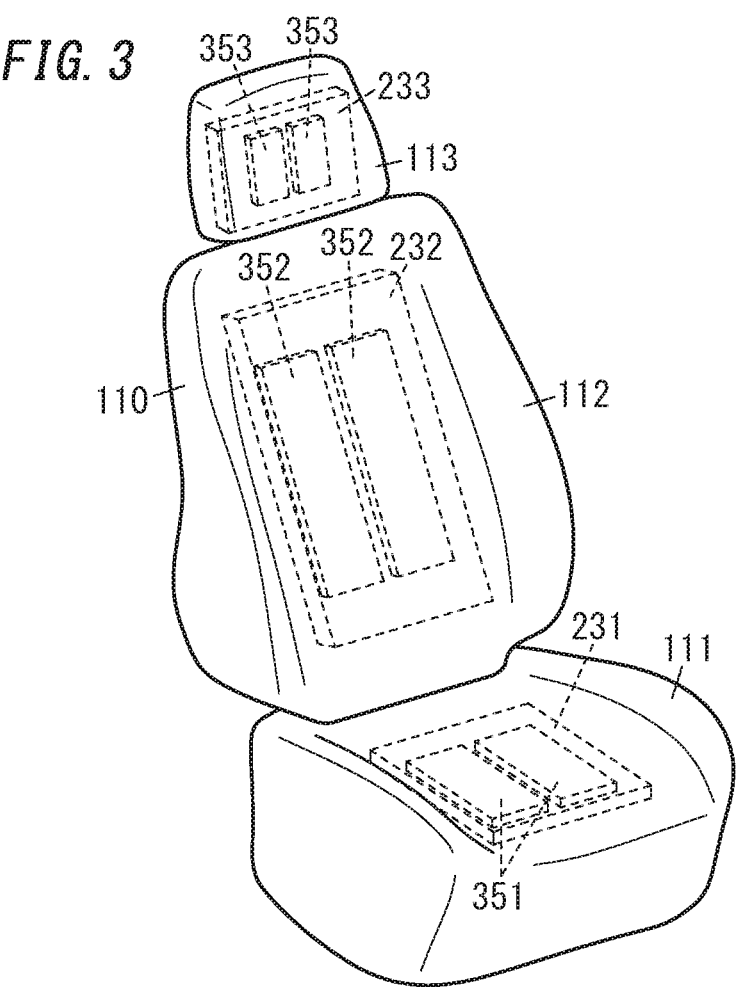
FIG. 3 illustrates a seat of the moving vehicle.
Figure 4:
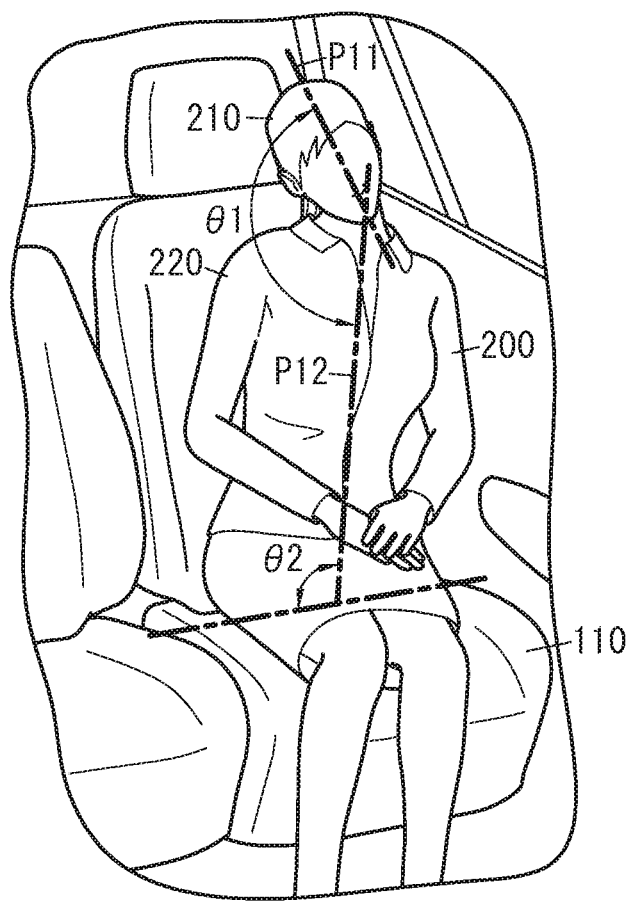
FIG. 4 illustrates how the travel sickness estimation system performs estimation processing.

The pressure sensor 23 is used to acquire the posture information. The pressure sensor 23 is installed in each of the seats 110 of the car 100. For example, the pressure sensor 23 may include a first pressure sensor 231, a second pressure sensor 232, and a third pressure sensor 233 as shown in FIG. 3. The first pressure sensor 231 is installed under the bearing surface 111 of the seat 110 to detect the center of gravity of the person 200. In this manner, the first pressure sensor 231 detects the center of gravity of the person 200 and the distribution of pressures applied by the person 200 to the moving vehicle 100. The output of the first pressure sensor 231 is used to calculate a tilt angle $\theta 1$ defined by the center axis P11 of the person's 200 head 210 with respect to center axis P12 of his or her body trunk 220 and a tilt angle $\theta 2$ defined by the center axis P12 with respect to a horizontal plane as shown in FIG. 4. These tilt angles $\theta 1$ and $\theta 2$ of the person 200 are used to evaluate the person's posture. The second pressure sensor 232 and the third pressure sensor 233 are installed in the backrest 112 and a headrest 113, respectively, to detect the distribution of pressures applied by the person 200 to the moving vehicle 100. Among other things, the second pressure sensor 232 is used to improve the accuracy of measurement of the center axis P12 of the person's 200 body trunk 220 (see FIG. 4). Meanwhile, the third pressure sensor 233 is used to improve the accuracy of measurement of the center axis P11 of the person's 200 head 210 (see FIG. 4).

The camera 24, the infrared sensor 25, the millimeter wave sensor 26, and the terahertz wave sensor 27 together form a sensor unit 29. The sensor unit 29 is installed on the roof 130 of the car 100 as shown in FIG. 2. Alternatively, the sensor unit 29 may be installed in the dashboard 120, not on the roof 310. Optionally, the millimeter wave sensor 26 and the terahertz wave sensor 27 may be installed separately in a line of sight for the passenger (i.e., the person 200 who is on board the car 100). At this time, only an RF circuit section, including an antenna, of the millimeter wave sensor 26 and the terahertz wave sensor 27 may be installed in a line of sight for the passenger.

The camera 24 is used to generate an image of the person 200 (in particular, an image representing the person's 200 head 210). The person's 200 image generated by the camera 24 is used to acquire the posture information. That is to say, the image generated by the camera 24 is used to calculate the tilt angles $\theta 1$, $\theta 2$ of the person 200. In addition, the camera 24 is also used to acquire the emotion information. That is to say, the person's 200 image generated by the camera 24 is used to determine the person's 200 emotions.

The infrared sensor 25 may be implemented as an infrared image sensor, in particular, to generate a thermal image of the person 200. The output (thermal image) of the infrared sensor 25 is used to acquire a variation in body temperature particular, the nose temperature), which is one piece of progress information. In addition, the thermal image generated by the infrared sensor 25 is also used to acquire the posture information. That is to say, the thermal image is used to calculate the tilt angles θ1, θ2 of the person 200. Moreover, the infrared sensor 25 is further used to acquire the emotion information. That is to say, the thermal image is used to determine the person's 200 emotions.

The millimeter wave sensor 26 and the terahertz wave sensor 27 detect a frequency caused by the person's 200 body movement. A heartbeat variation spectrum (heartbeat fluctuation spectrum) is obtained based on the respective outputs of the millimeter wave sensor 26 and the terahertz wave sensor 27. This heartbeat variation spectrum may be divided into a low frequency component falling within the band from about 0.05 Hz to about 0.15 Hz and a high frequency component falling within the band from about 0.15 Hz to about 0.8 Hz. The low frequency component is affected by a modulation in the activity of sympathetic and parasympathetic nervous systems due to the feedback control of blood pressures. The low frequency component of the heartbeat variation spectrum includes a component deriving from a variation in blood pressure (blood pressure component). On the other hand, the high frequency component of the heartbeat variation spectrum includes a component deriving from respiration (respiration component). A peak frequency of this respiration component would be the respiration frequency. In view of these considerations, the millimeter wave sensor 26 and the terahertz wave sensor 27 are used in combination to acquire the progress information. The progress information acquired by the millimeter wave sensor 26 and the terahertz wave sensor 27 indicates variations in heartbeat and respiration. Sensors with directivity may be used as the millimeter wave sensor 26 and the terahertz wave sensor 27. In that case, the millimeter wave sensor 26 and the terahertz wave sensor 27 are able to acquire a frequency component from a space where the person 200 is present and a frequency component from a space where the person 200 is absent. Calculating the difference between the frequency component from the space where the person 200 is present and the frequency component from the space where the person 200 is absent allows the noise caused by the shake of the moving vehicle (car 100), for example, to be reduced. This allows the millimeter wave sensor 26 and the terahertz wave sensor 27 to measure the frequency components more accurately. Optionally, the directivities of the millimeter wave sensor 26 and the terahertz wave sensor 27 may be controlled either mechanically by controlling the orientation of the antenna or electronically using an array antenna. Alternatively, the millimeter wave sensor 26 and the terahertz wave sensor 27 may be replaced with a microwave sensor as well. In short, any appropriate frequency sensor may be used without limitation.

The breath sensor 28 is a gas sensor for detecting a gas included in the person's 200 breath. The breath sensor 28 is used acquire the progress information. The progress information acquired by the breath sensor 28 is a variation in breath. Examples of the gases detected by the breath sensor 28 include a gas (such as carbon dioxide) that has something to do with travel sickness. A decrease in the concentration of carbon dioxide in breath is considered a sign of the onset of travel sickness. Examples of the gases detected by the breath sensor 28 further include gases (such as aldehyde-based gases and pyrrole-based gases) that have something to do with emotions (such as stress). They believe that there is positive correlation between the concentration of an aldehyde-based or pyrrole-based gas and the emotion (stress). For example, when the concentration of aldehyde increases, a determination may be made that the stress should be mounting. As shown in FIG. 2, the breath sensor 28 is provided for a front portion of the headrest 113 of the front seat 110 and behind the headrest 113. The breath sensor 28 provided for the front portion of the headrest 113 is used to detect the breath of the person 200 seated on the front seat 110. The breath sensor 28 provided behind the headrest 113 is used to detect the breath of another person 200 seated on a rear seat 110.

The device system 30 includes a loudspeaker 31, a car navigation system 32, an air conditioner 33, a power window 34, a driving unit 35, an odor control device 36, a relaxation device 37, a traveling controller 38, and a cooling device 39 as shown in FIG. 1. The loudspeaker 31, the car navigation system 32, the air conditioner 33, the power window 34, the driving unit 35, the odor control device 36, the relaxation device 37, the traveling controller 38, and the cooling device 39 are all installed in the body 101.

The loudspeaker 31, the car navigation system 32, the air conditioner 33, and the power window 34 are pieces of onboard equipment of the car 100. The loudspeaker 31 is an apparatus for reproducing sounds, music, and other types of audio data. The car navigation system 32 is a system for helping the driver navigate the car 100 to his or her destination, for example. Some car navigation systems 32 may include a 3D head-up display (HUD), for example, to display information by projecting a virtual image into the person's 200 sight. Such a virtual image tends to cause travel sickness for the person 200 more easily than an image displayed on a liquid crystal display. The air conditioner 33 is a device for controlling the temperature inside the car 100. The power window 34 is a device for opening and closing the car 100 windows. The functions of the loudspeaker 31, the car navigation system 32, the air conditioner 33, and the power window 34 are well known in the art, and detailed description thereof will be omitted herein.

The driving unit 35 is installed in the seat 110 of the moving vehicle (car 100) and has the capability of changing the surface shape of the seat 110. The driving unit 35 urges the person 200 seated on the seat 110 to change his or her posture by changing the surface shape of the seat 110. As shown in FIG. 3, the driving unit 35 includes a pair of first actuators 351, a pair of second actuators 352, and a pair of third actuators 353. The pair of first actuators 351 is provided for the bearing surface Iii of the seat 110 to be arranged side by side in the rightward/leftward direction with respect to the bearing surface 111. Each of these first actuators 351 changes the shape of the bearing surface 111 by driving an arm with a power source (such as an air pack or a motor) and thereby applying pressure to the bearing surface 111 from its inside to outside. The pair of first actuators 351 may be controlled on an individual basis. This allows the bearing surface 111 to be tilted either to the right or to the left. In addition, the pair of first actuators 351 may also have their tilt angle controlled on an individual basis in the forward/backward direction. This allows the bearing surface 111 to be tilted either forward or backward. The pair of second actuators 352 is provided for the backrest 112 of the seat 110 to be arranged side by side in the rightward/leftward direction with respect to the backrest 112. Each of these second actuators 352 changes the surface shape of the backrest 112 by driving an arm with a power source (such as an air pack or a motor) and thereby applying pressure to the backrest 112 from its inside to outside. The pair of second actuators 352 may be controlled on an individual basis. This allows the surface of the backrest 112 to be tilted either to the right or to the left. In addition, the pair of second actuators 352 may also have their tilt angle controlled on an individual basis in the upward/downward direction. This allows the backrest 112 to be tilted either upward or downward. The pair of third actuators 353 is provided for the headrest 113 of the seat 110 to be arranged side by side in the rightward/leftward direction with respect to the headrest 113. Each of these third actuators 353 changes the surface shape of the headrest 113 by driving an arm with a power source (such as an air pack or a motor) and thereby applying pressure to the headrest 113 from its inside to outside. The pair of third actuators 353 may be controlled on an individual basis. This allows the surface of the headrest 113 to be tilted either to the right or to the left. In addition, the pair of third actuators 353 may also have their tilt angle controlled on an individual basis in the upward/downward direction. This allows the surface of the headrest 113 to be tilted either upward or downward. In addition, the driving unit 35 also has the capability of adjusting the angle defined by the backrest 112 of the seat 110 with respect to the bearing surface 111 thereof. In this embodiment, the driving unit 35 is a device for driving the seat 110. In this embodiment, the driving unit 35 is provided for each seat 110 of the car 100.

The odor control device 36 has a component for controlling the odor in the car 100. In this embodiment, the odor control device 36 is configured to exhale a component for controlling the odor in the car 100. Examples of such components for controlling the odor include deodorant components (deodorizers) and aromatic components (air freshener) The odor control device 36 may diffuse such an odor control component inside the car 100 by exhaling the odor control component through an air outlet of the air conditioner 33, for example. Alternatively, the odor control device 36 may also exhale such an odor control component directly toward the person 200. Exhaling the odor control component directly toward the person 200 allows the odor to be controlled only around the person 200 who is likely to have travel sickness. Optionally, the odor control device 36 may also have, as a deodorant component, a component for adsorbing the odor. In that case, the odor control device 36 does not have to exhale such a deodorant component but just needs to have the deodorant component mixed with the air in the car 100 while the odor needs to be controlled.

The relaxation device 37 is a device for producing a relaxation effect on the person 200. In this embodiment, the relaxation device 37 produces the relaxation effect by using the loudspeaker 31, the air conditioner 33, the power window 34, the driving unit 35, and the odor control device 36. The relaxation device 37 produces the relaxation effect by playing music through the loudspeaker 31. The music is suitably as a musical tune that has a relaxation effect or the person's 200 favorite musical tune. In addition, the relaxation device 37 also produces the relaxation effect by conditioning the air in the internal space of the car 100 to comfortable one using the air conditioner 33. For example, the relaxation device 37 may create warm air at a comfortable temperature for the person 200 in the internal space of the car 100. That is to say, the relaxation device 37 controls the conditions of the air inside the car 100 according to the person's 200 physical conditions (such as his or her body temperature). Furthermore, the relaxation device 37 may also produce the relaxation effect by letting outdoor air in by opening the windows using the power window 34. Furthermore, the relaxation device 37 may also produce the relaxation effect by massaging the person 200 seated on the seat 110 using the driving unit 35 and thereby relaxing his or her muscles. Furthermore, the relaxation device 37 may also produce the relaxation effect by adjusting the angle of the backrest 112 using the driving unit 35. Moreover, the relaxation device 37 further produces the relaxation effect by having the odor control device 36 exhale an aromatic component.

The traveling controller 38 is a device for controlling the car's 100 traveling. The traveling controller 38 has the capability of automatically controlling the speed of the car 100. Thus, the traveling controller 38 allows the car 100 to either slow down or stop irrespective of the car 100 driver's operations.

The cooling device 39 is configured to cool a part of the person's 200 body. Examples of parts of the body include his or her neck or part between his or her legs. The cooling device 39 may include Peltier elements provided for the bearing surface 111 of the seat 110 and the headrest 113. Alternatively, the cooling device 39 may also cool a part of the person's 200 body by any known cooling method such as water cooling or air cooling. Still alternatively, the air conditioner 33 may also be used as the cooling device 39. Yet alternatively, a cooling fan provided for the seat 110 may also be used as the cooling device 39. Optionally, the cooling device 39 does not have to be a single cooling device but may also be a system including a plurality of cooling devices. For example, the cooling device 39 may include a Peltier element, an air cooling fan, and an air conditioner. This allows the person's 200 body to be cooled at an increased rate.

As shown in FIG. 1, the controller 40 includes a processing unit 41 and a communications unit 42.

The communications unit 42 is provided to acquire information from external devices. In this embodiment, the external devices include a data center 50 and a telecommunications device 60. That is to say, the controller 40 may be connected to, and is able to communicate with, the data center 50 and the telecommunications device 60 via the communications unit 42. The communications unit 42 is a communications interface to establish communication over a communications network. The communications unit 42 is compliant with a communications protocol compatible with communication over a communications network. The communications network does not have to be a network compliant with a single communications protocol but may also be made up of a plurality of networks compliant with multiple different communications protocols. The communications protocol may be selected from various known wired and wireless communications standards. Nevertheless, the communications between the communications unit 42 and the external devices is suitably established via mobile communication. Note that the communications network may include, as needed, any of various data communications devices such as a repeater hub, a switching hub, a bridge, a gateway, and a router.

In this case, the data center 50 is a device for collecting information about travel sickness. The data center 50 may include, for example, a server for collecting information about travel sickness from a plurality of moving vehicles and a device installed in the moving vehicle itself to collect information about travel sickness from the moving vehicle. Such information collected by the data center 50 about travel sickness may be used to improve the accuracy of the estimation processing.

The telecommunications device 60 may be, for example, a smartphone, a tablet computer, or any other mobile telecommunications device owned by the person 200 who is on board the car 100.

The processing unit 41 may be implemented as one or more processors (microprocessors) and one or more memories. That is to say, the one or more processors function as the processing unit 41 by executing one or more programs stored in the one or more memories. The one or more programs may be stored in advance in the memory. Alternatively, the one or more programs may also be downloaded via a telecommunications line such as the Internet or distributed after having been stored in a non-transitory storage medium such as a memory card.

The processing unit 41 includes an input unit 411, an estimation unit 412, an output unit 413, a notification unit 414, a control unit 415, and a storage unit 416 as shown in FIG. 1. Note that none of the input unit 411, the estimation unit 412, the output unit 413, the notification unit 414, the control unit 415, and the storage unit 416 have a substantive configuration but these units 411-416 represent various functions performed by the processing unit 41.

The input unit 411 is configured to receive the output of the sensing system 20. The output of the sensing system 20 includes the respective outputs of the acceleration sensor 21a, the angular velocity sensor 21b, the odor sensor 22, the pressure sensor 23, the camera 24, the infrared sensor 25, the millimeter wave sensor 26, the terahertz wave sensor 27, and the breath sensor 28, all of which are included in the sensing system 20.

The estimation unit 412 is configured to perform estimation processing of estimating, based on person information indicating the conditions of the person 200 who is on board the moving vehicle (car 100), whether or not the person 200 is in circumstances that would cause travel sickness for him or her. The estimation unit 412 is configured to perform the estimation processing with reference to not only the person information but also moving vehicle information indicating the conditions of the moving vehicle (car 100). That is to say, the estimation unit 412 performs the estimation processing of estimating, with reference to the person information and the moving vehicle information, whether or not the person 200 is in circumstances that would cause travel sickness for him or her.

Before performing the estimation processing, the estimation unit 412 acquires the person information and the moving vehicle information.

The estimation unit 412 acquires the person information based on the respective outputs of the pressure sensor 23, the camera 24, the infrared sensor 25, the millimeter wave sensor 26, the terahertz wave sensor 27, and the breath sensor 28. The person information includes the posture information, the progress information, and the emotion information as described above.

To acquire the posture information, the estimation unit 412 uses the pressure sensor 23, the camera 24, and the infrared sensor 25. That is to say, the estimation unit 412 acquires the posture information based on the respective outputs of the pressure sensor 23, the camera 24, and the infrared sensor 25. In this embodiment, the person's 200 posture indicated by the posture information is represented by the tilt angles $\theta1$, $\theta2$ defined by the person 200. The estimation unit 412 obtains the tilt angles $\theta1$, $\theta2$ based on the person's 200 center of gravity detected by the pressure sensor 23 and the distribution of pressures applied by the person 200 to the moving vehicle 100. In this embodiment, the estimation unit 412 determines the tilt angles $\theta1$, $\theta2$ finally by correcting, based on the respective outputs of the camera 24 and the infrared sensor 25, the tilt angles $\theta1$, $\theta2$ that have been once obtained.

To obtain the emotion information, the estimation unit 412 uses the camera 24 and the infrared sensor 25. That is to say, the estimation unit 412 acquires the emotion information based on the respective outputs of the camera 24 and the infrared sensor 25. In this embodiment, the person's 200 emotion indicated by the emotion information is represented by a stress value. The estimation unit 412 determines the stress value according to the person's 200 emotions estimated by the expression of the person 200 captured in the output (image) of the camera 24. For example, the estimation unit 412 classifies the person's 200 expressions into five categories (namely, pleased, surprised, angry, sad, and straight face expressions). For example, the stress value may be set at a reference value when the person 200 is putting on a surprised or straight face expression. The stress value is higher than the reference value when he or she gives an angry or sad expression and is lower than the reference value when he or she looks pleased. In addition, the estimation unit 412 also estimates the person's 200 emotion by the face temperature of the person 200 captured in the output (thermal image) of the infrared sensor 25. For example, when finding the face temperature of the person 200 high, the estimation unit 412 sets the stress value at an increased value. On the other hand, when finding the face temperature of the person 200 low, the estimation unit 412 sets the stress value at a decreased value. In this manner, the estimation unit 412 determines the stress value representing the person's 200 emotions.

To acquire the progress information, the estimation unit 412 uses the infrared sensor 25, the millimeter wave sensor 26, the terahertz wave sensor 27, and the breath sensor 28. That is to say, the estimation unit 412 acquires the progress information based on the respective outputs of the infrared sensor 25, the millimeter wave sensor 26, the terahertz wave sensor 27, and the breath sensor 28. The progress information includes a variation in body temperature (in particular, the nose temperature) obtained based on the output of the infrared sensor 25, variations in heartbeat and respiration obtained based on the respective outputs of the millimeter wave sensor 26 and the terahertz wave sensor 27, and a variation in breath obtained based on the output of the breath sensor 28.

In this embodiment, the pressure sensor 23, the camera 24, the infrared sensor 25, the millimeter wave sensor 26, the terahertz wave sensor 27, and the breath sensor 28 for acquiring the person information are provided for each seat 110 of the car 100. Thus, when a plurality of persons 200 are on board the car 100, the estimation unit 412 performs the estimation processing on each of the plurality of persons 200 on an individual basis.

The estimation unit 412 acquires the moving vehicle information based on the respective outputs of the acceleration sensor 21a, the angular velocity sensor 21h, and the odor sensor 22. The moving vehicle information includes the behavior information and the atmosphere information as described above. The behavior information includes information about various types of car's 100 behaviors including its turning direction, turning speed, traveling direction, and propulsion. The atmosphere information includes information about an odor as the atmosphere in the internal space of the car 100. The odor is represented as the concentration of a gas detected by the odor sensor 22.

In this manner, the estimation unit 412 acquires condition information including the posture information (represented by the tilt angles $\theta1$, $\theta2$), the emotion information (represented by the first and second stress values), and progress information (represented by variations in body temperature, heartbeat, respiration, and breath). In addition, the estimation unit 412 also acquires moving vehicle information including the behavior information (about the car's 100 traveling direction and propulsion) and the atmosphere information (about the concentration of a gas).

In performing the estimation processing, the estimation unit 412 determines, based on an estimated value about travel sickness, whether or not the person 200 is in circumstances that would cause travel sickness for him or her. When finding the estimated value about travel sickness to be equal to or greater than a preset threshold value, the estimation unit 412 determines that the person 200 should be in circumstances that would cause travel sickness for him or her. On the other hand, when finding the estimated value about travel sickness to be less than the preset threshold value, the estimation unit 412 determines that the person 200 should not be in circumstances that would cause travel sickness for him or her.

The estimated value about travel sickness may be determined by the following six Factors (1) to (6):

Factor (1) includes the tilt angles $\theta 1$, $\theta 2$ and the car's 100 traveling direction and propulsion. The person's posture (represented by the tilt angles $\theta 1$, $\theta 2$) varies behindhand according to the car's 100 behavior (including the traveling direction and the propulsion), which constitutes a factor in an increase in the estimated value about travel sickness. Particularly when finding the tilt angle $\theta 1$, $\theta 2$ or the car's 100 traveling direction or propulsion greater than their reference value, the estimation unit 412 obtains the magnitude of the gap between the car's 100 behavior and the person's posture to increase the estimated value according to the magnitude of the gap. Therefore, when the magnitudes of the gap between the car's 100 behavior and the person's posture are accumulated to make the estimated value about travel sickness equal to or greater than the threshold value, a determination is made that the person 200 should be in circumstances that would cause travel sickness for him or her.

Factor (2) is a variation in body temperature. It is known that when a person suffers travel sickness, his or her body temperature (his or her nose temperature, in particular) decreases. Thus, the sign of a decrease in body temperature constitutes a factor in an increase in the estimated value about travel sickness.

Factor (3) is a gas concentration. In this embodiment, the gas concentration is the concentration of a gas that tends to trigger the onset of travel sickness for the person 200. Thus, a gas concentration being equal to or greater than a reference value constitutes a factor in an increase in the estimated value about travel sickness.

Factor (4) is a variation in breath. In this embodiment, a variation in breath represents a variation in the concentration of carbon dioxide ($CO_2$) in the breath. It is known that a person who is suffering travel sickness just lightly should take a breath with a high $CO_2$ concentration. Thus, the concentration of $CO_2$ in the breath being equal to or less than a reference value constitutes a factor in an increase in the estimated value about travel sickness.

Factor (5) includes first and second stress values. A person under heavy mental stress would suffer travel sickness relatively easily. Thus, an increase in stress values constitutes a factor in an increase in the estimated value about travel sickness.

Factor (6) includes variations in heartbeat and respiration. It is known that a person who is suffering travel sickness comes to have a higher respiration frequency. Thus, an increase in respiration frequency constitutes a factor in an increase in the estimated value about travel sickness. The determination about Whether or not the respiration frequency has increased may be made by seeing if the respiration frequency has become equal to or greater than a threshold value. Alternatively, the determination about whether or not the respiration frequency has increased may be made by seeing if the heartbeat frequency has become equal to or greater than a reference value without causing an increase in heartbeat component. Still alternatively, the determination about whether or not the respiration frequency has increased may be made by seeing if the ratio of a high frequency component of a heartbeat variation spectrum to a low frequency component thereof has become equal to or greater than a reference value.

In this manner, in performing the estimation processing, the estimation unit 412 determines, based on the estimated value about travel sickness, whether or not the person 200 is in circumstances that would cause travel sickness for him or her. In this case, the threshold value with respect to the estimated value about travel sickness may vary from one person 200 to another. The threshold value may be set appropriately via experiment, for example. Setting the threshold value appropriately would improve the accuracy of estimation by the estimation processing. Likewise, the reference values for Factors (3), (4), and (6) may also vary from one person 200 to another. These reference values may be set appropriately via experiment, for example. Setting the reference values appropriately would improve the accuracy of estimation by the estimation processing.

The output unit 413 outputs the results of the estimation processing by the estimation unit 412 to the notification unit 414 and the control unit 415.

The notification unit 414 receives the result of the estimation processing from the output unit 413. If the result of the estimation processing indicates that the person 200 is in circumstances that would cause travel sickness for him or her, then the notification unit 414 performs notification processing of notifying the person 200 of the chances of the onset of travel sickness. On the other hand, if the result of the estimation processing that the notification unit 414 has received after having performed the notification processing does not indicate that the person 200 is in circumstances that would cause travel sickness for him or her, then the notification unit 414 ends the notification processing.

The notification unit 414 establishes a notification system in cooperation with a particular device included in the device system 30. The notification system is a system for notifying the person 200 who is on board the car 100 of the chances of the onset of travel sickness. In this embodiment, the notification system includes not only the notification unit 414 but also the loudspeaker 31 and the car navigation system 32. The notification unit 414 performs the notification processing using the loudspeaker 31 and the car navigation system 32. In performing the notification processing, the notification unit 414 notifies the person 200 of the chances of the onset of travel sickness by making the loudspeaker 31 and the car navigation system 32 emit a verbal message (verbal announcement). The verbal message (vertical announcement) may be a message prompting the person 200 to stop his or her ongoing activity (such as reading a book, playing a game, or operating a PC). This urges him or her to take precautions against travel sickness such as closing his or her eyes or lying down on the seat. Optionally, the notification unit 414 may use an alarm sound such as a buzz with or without a warning message (warning announcement) displayed as a sentence on the screen.

The control unit 415 receives the result of the estimation processing from the output unit 413. If the result of the estimation processing indicates that the person 200 is in circumstances that would cause travel sickness for him or her, then the control unit 415 performs prevention processing of preventing the person 200 from suffering travel sickness. If the result of the estimation processing that the control unit 415 receives after having performed the prevention processing does not indicate that the person 200 is in circumstances that would cause travel sickness for him or her, then the control unit 415 ends the prevention processing. In this embodiment, if a plurality of persons 200 are on board the car 100, the estimation unit 412 performs the estimation processing on each of the plurality of persons 200 on an individual basis. Thus, the control unit 415 determines, based on the result of the estimation processing performed on each of the plurality of persons 200, whether or not to perform the prevention processing on each of the plurality of persons 200 on an individual basis. Therefore, if a plurality of persons 200 are on board the car 100, the control unit 415 performs the prevention processing on each of the plurality of persons 200 on an individual basis.

The control unit 415 establishes a prevention system in cooperation with a particular device included in the device system 30. The prevention system is a system for preventing the onset of travel sickness for the person 200 who is on board the car 100. In this embodiment, the prevention system includes not only the control unit 415 but also the loudspeaker 31, the car navigation system 32, the air conditioner 33, the power window 34, the driving unit 35, the odor control device 36, the relaxation device 37, the traveling controller 38, and the cooling device 39. The control unit 415 performs the prevention processing by using the loudspeaker 31, the car navigation system 32, the air conditioner 33, the power window 34, the driving unit 35, the odor control device 36, the relaxation device 37, the traveling controller 38, and the cooling device 39.

In performing the prevention processing, the loudspeaker 31 emits a verbal message (verbal announcement) recommending the person 200 to take a break without hesitation.

In performing the prevention processing, the car navigation system 32 changes the route to the car's 100 destination to relieve the burden on the person 200. That is to say, the prevention processing includes changing the route to the car's 100 destination into a route that reduces the chances of the onset of travel sickness for the person 200. For example, the route to the car's 100 destination may be changed from a route passing through mountain roads into a route passing through a downtown. In addition, in performing the prevention processing, the car navigation system 32 also controls the image presented on the display of the car navigation system 32 or the HUD to relieve the burden on the person 200. For example, the car navigation system 32 may move (up, down, to the right or left, or forward or backward) or rotate the image according to the person's 200 body movement. Optionally, the car navigation system 32 may also calculate the person's 200 height and weight using the pressure sensor 23 to display an appropriate relief from travel sickness and recommend him or her to take that relief. This allows the type and dosage of the relief to be determined. That is to say, a determination may be made whether the person 200 should take a relief for kids or a relief for adults and how much he or she should take the relief.

In performing the prevention processing, the relaxation device 37 uses the air conditioner 33 and the power window 34 to produce the relaxation effect.

In performing the prevention processing, the driving unit 35 changes the surface shape of the seat 110 to relieve the burden on the person 200. For example, the driving unit 35 controls the respective tilt angles of the head 210 and body trunk 220 of the person 200 according to at least one of the acceleration or angular velocity of the car 100 by driving the first, second, and third actuators 351, 352, 353. Specifically, the driving unit 35 drives the first, second, and third actuators 351, 352, 353 so as to reduce the gap between the car's 100 behavior and the person's posture.

In performing the prevention processing, the odor control device 36 exhales deodorant components (deodorizers). This allows the odor control device 36 to reduce the chances of the onset of travel sickness for the person 200 by decreasing the concentration of a gas that tends to trigger the onset of travel sickness for him or her.

In performing the prevention processing, the relaxation device 37 produces the relaxation effect on the person 200. The relaxation effect may be produced by the method described above.

In performing the prevention processing, the traveling controller 38 controls the car's 100 traveling in such a manner as to relieve the burden on the person 200. For example, the traveling controller 38 may slow down the car 100, thus relieving the burden on the person 200 due to the car's 100 behavior. Alternatively, the traveling controller 38 may bring the car 100 to a stop at a safe place (such as a rest area (so-called "service area" in Japan) or a parking lot). In addition, in performing the prevention processing, the traveling controller 38 changes the specifics of control of the moving vehicle (car 100) according to the remaining traveling time that it takes for the moving vehicle (car 100) to arrive at its destination. For example, when finding the remaining traveling time to the destination equal to or longer than a predetermined amount of time, the traveling controller 38 determines that the car 100 should be unable to arrive at the destination before the person 200 has travel sickness, and therefore, slows down the moving vehicle (car 100). On the other hand, when finding the remaining traveling time to the destination less than the predetermined amount of time, the traveling controller 38 determines that the car 100 should be able to arrive at the destination before the person 200 has travel sickness, and therefore, does not change the speed of the moving vehicle (car 100).

In performing the prevention processing, the cooling device 39 cools a part of the person's 200 body. For example, the cooling device 39 may rapidly cool the person's 200 neck or part between his or her legs (and suitably rapidly cool a rear part of his or her neck) using Peltier elements provided under the bearing surface 111 of the seat 110 and under the headrest 113. This would produce the action of balancing between the parasympathetic nervous system and the sympathetic nervous system by inhibiting the activity of the parasympathetic nervous system, thus reducing the chances of the onset of travel sickness for the person 200. In this case, the magnitude of the decrease caused by the cooling device 39 in the temperature of that part of the person's 200 body may be determined based on clinical data about the person's travel sickness, for example.

In performing the prevention processing, the control unit 415 does not have to use all of the loudspeaker 31, the car navigation system 32, the air conditioner 33, the power window 34, the driving unit 35, the odor control device 36, the relaxation device 37, the traveling controller 38, and the cooling device 39. The control unit 415 changes the specifics of the prevention processing according to the estimated value about travel sickness. For example, when finding the estimated value about travel sickness equal to or greater than a threshold value but less than a preset value, the control unit 415 may instruct the traveling controller 38 to slow down the car 100. On the other hand, when finding the estimated value about travel sickness equal to or greater than the preset value, the control unit 415 may instruct the traveling controller 38 to bring the car 100 to a stop. That is to say, in performing the prevention processing, the control unit 415 may begin with a type of processing that would achieve relatively less significant travel sickness prevention effect, and may change, when finding the travel sickness prevention effect insufficient, the type of processing into the one that would achieve more significant travel sickness prevention effect.

The storage unit 416 stores an estimation algorithm for determining the specifics of the estimation processing to be performed by the estimation unit 412 (hereinafter referred to as a "travel sickness estimation program"). In this embodiment, the controller 40 may acquire information about travel sickness from the data center 50. Thus, the estimation unit 412 corrects, based on the information acquired from the data center 50 (i.e., the information about travel sickness), the estimation algorithm stored in the storage unit 416. Examples of the information about travel sickness include road information (about the degree of roughness of the road surface and the radius of curvature of the curves) of the roads that the car 100 is going to travel along. If the degree of roughness of the surface of the road that the car 100 is going to travel along is significant, then it would increase the chances of the onset of travel sickness for the person 200. In that case, the estimation unit 412 lowers the threshold value of the estimated value about travel sickness for use in the estimation processing to increase the chances of the result of the estimation processing indicating that the person 200 is in circumstances that would cause travel sickness for him or her.

In the travel sickness estimation system 10 described above, the controller 40 includes the estimation unit 412 and the output unit 413. The controller 40 is implemented as a combination of one or more processors and one or more memories. That is to say, the function of the controller 40 is performed by making the one or more processors execute a program (i.e., the travel sickness estimation program). When executed by the one or more processors, the travel sickness estimation program gives the one or more processors a first instruction and a second instruction. The first instruction is an instruction to perform the estimation processing of estimating, based on person information indicating the conditions of the person 200 who is on board the moving vehicle (car 100), whether or not the person 200 is in circumstances that would cause travel sickness for him or her. The second instruction is an instruction to output the result of the estimation processing. Such a travel sickness estimation program, as well as the travel sickness estimation system 10, also reduces the onset of travel sickness.

In other words, it can be said that the controller 40 is performing the following travel sickness estimation method. The travel sickness estimation method includes a first step and a second step. The first step includes performing estimation processing of estimating, based on person information indicating the conditions of the person 200 who is on board the moving vehicle (car 100), whether or not the person 200 is in circumstances that would cause travel sickness for him or her. The second step includes outputting the result of the estimation processing. Such a travel sickness estimation method, as well as the travel sickness estimation system 10, also reduces the onset of travel sickness.

1.3. Operation

Figure 5:
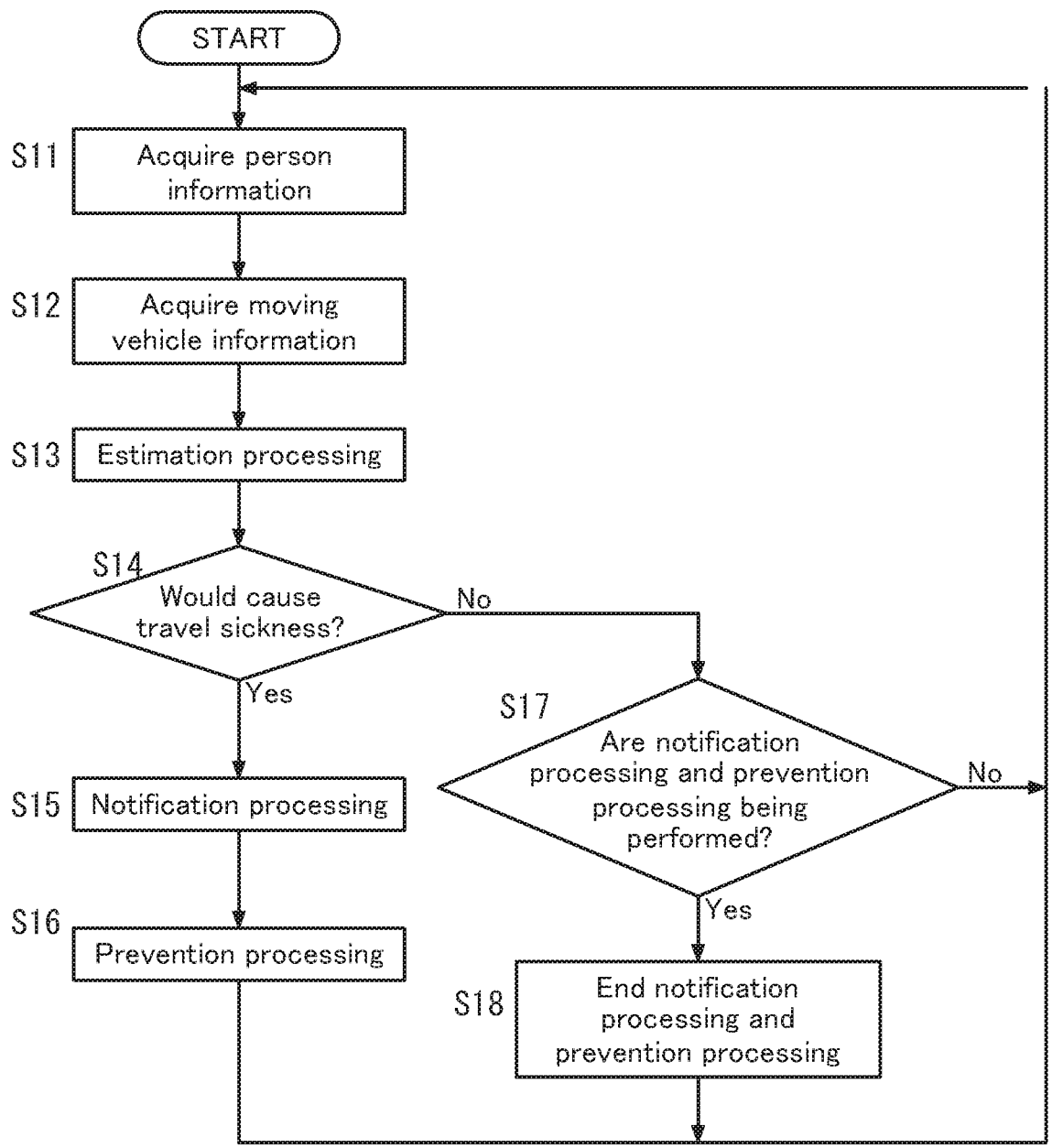
FIG. 5 is a flowchart showing the procedure of operation of the travel sickness estimation system.

Next, an exemplary operation of the travel sickness estimation system 10 will be described briefly with reference to the flowchart shown in FIG. 5.

First, the estimation unit 412 acquires, based on the output of the sensing system 20 obtained via the input unit 411, person information and moving vehicle information (in S11 and S12, respectively). Next, the estimation unit 412 performs the estimation processing of estimating, based on the person information and the moving vehicle information, whether or not the person 200 is in circumstances that would cause travel sickness for him or her (in S13). The result of the estimation processing is forwarded by the output unit 413 to the notification unit 414 and the control unit 415. If the result of the estimation processing indicates that the person 200 is in circumstances that would cause travel sickness for him or her (if the answer is YES in S14), the notification system performs the notification processing (in S15) and the prevention system performs the prevention processing (in S16). On the other hand, if the result of the estimation processing does not indicate that the person 200 is in circumstances that would cause travel sickness for him or her (if the answer is NC) in S14) and the notification processing and the prevention processing are being performed (if the answer is YES in S17), then the notification processing and the prevention processing are to be ended (in S18). On the other hand, if neither the notification processing nor the prevention processing is being performed (if the answer is NO in S17), then the process goes back to the step SU.

As can be seen from the foregoing description, when it is estimated that the person 200 is in circumstances that would cause travel sickness for him or her, the travel sickness estimation system 10 according to this embodiment performs the notification processing and the prevention processing. This allows the travel sickness estimation system 10 to reduce the chances of the onset of travel sickness. In addition, the notification processing and the prevention processing are performed only when it is estimated that the person 200 is in circumstances that would cause travel sickness for him or her. This reduces the chances of making the person 200 uncomfortable by performing the notification and prevention when neither the notification nor the prevention is required or even triggering the onset of travel sickness to the contrary.

2. Variations

Note that the embodiment described above is only an example of the present disclosure and should not be construed as limiting. Rather, the embodiment may be readily modified in various manners depending on a design choice or any other factor without departing from a scope of the present disclosure. Next, variations of the embodiment described above will be enumerated one after another.

According to one variation, the prevention system may be configured to perform the prevention processing if the result of the estimation processing still indicates, even after the notification system has performed the notification processing, that the person 200 is in circumstances that would cause travel sickness for him or her.

Next, an exemplary operation of the travel sickness estimation system 10 according to this variation will be described briefly with reference to the flowchart shown in FIG. 6.

First, the estimation unit 412 acquires, based on the output of the sensing system 20 that has been obtained via the input unit 411, person information and moving vehicle information (in S21 and S22, respectively). Next, the estimation unit 412 performs the estimation processing of estimating, based on the person information and the moving vehicle information, whether or not the person 200 is in circumstances that would cause travel sickness for him or her (in S23). The result of the estimation processing is forwarded by the output unit 413 to the notification unit 414 and the control unit 415. If the result of the estimation processing indicates that the person 200 is in circumstances that would cause travel sickness for him or her (if the answer is YES in S24), a determination is made whether or not the notification processing is being performed (in S25). If the notification processing is not being performed (if the answer is NO in S25), the notification system performs the notification processing (in S26) and the process goes back to the step S21. Meanwhile, if the notification processing is being performed (if the answer is YES in S25), then the prevention system performs the prevention processing (in S27) and the process goes back to the step S21. On the other hand, if the result of the estimation processing does not indicate that the person 200 is in circumstances that would cause travel sickness for him or her (if the answer is NO in S24), a determination is made whether or not the notification processing is being performed (in S28). If the notification processing is not being performed (if the answer is NO in S28), the process goes back to the step S21. Meanwhile, if the notification processing is being performed (if the answer is YES in S28), then a determination is made whether or not the prevention processing is being performed (in S29). If the prevention processing is being performed (if the answer is YES in S29), the notification processing and the prevention processing end (in S30) and the process goes back to the step S21. Meanwhile, if the prevention processing is not being performed (if the answer is NO in S29), then the notification processing ends (in S31) and the process goes back to the step S21.

As can be seen from the foregoing description, when it is estimated that the person 200 is in circumstances that would cause travel sickness for him or her, the travel sickness estimation system 10 according to this variation performs the notification processing. Then, if it is still estimated, even after the notification processing has been performed, that the person 200 is in circumstances that would cause travel sickness for him or her, the travel sickness estimation system 10 performs the prevention processing. This allows the travel sickness estimation system 10 to reduce the onset of travel sickness. In addition, the prevention processing is performed only when it is still estimated, even after the notification processing has been performed, that the person 200 is in circumstances that would cause travel sickness for him or her. This reduces the chances of making the person 200 uncomfortable by performing the prevention when it is unnecessary or even triggering the onset of travel sickness to the contrary.

The sensing system 20 does not have to include all of the acceleration sensor 21a, the angular velocity sensor 21b, the odor sensor 22, the pressure sensor 23, the camera 24, the infrared sensor 25, the millimeter wave sensor 26, the terahertz wave sensor 27, and the breath sensor 28. The sensing system 20 may further include any other type of device as well. The sensing system 20 at least needs to be configured to acquire person information about the person 200. In addition, the pressure sensor 23 needs to detect at least one of the center of gravity of the person 200 or the distribution of the pressures applied by the person 200 to the moving vehicle (car 100). That is to say, the pressure sensor 23 does not have to detect both of these as in the embodiment described above. The pressure sensor 23 may consist of a single sensing element or include a plurality of sensing elements arranged in an array.

The device system 30 does not have to include all of the loudspeaker 31, the car navigation system 32, the air conditioner 33, the power window 34, the driving unit 35, the odor control device 36, the relaxation device 37, the traveling controller 38, and the cooling device 39. The device system 30 may further include any other type of device as well. For example, the device system 30 may include a bag supplier for automatically supplying a barf bag. In that case, when the prevention processing is performed, the bag supplier may automatically supply a barf bag to the person 200. Note that the barf bag suitably exhales an odor that would prevent travel sickness effectively (i.e., a fragrance such as a sweet smell of an air freshener that would relieve travel sickness). Optionally, the device system 30 may further include a drink and food supplier for automatically supplying a drink or a food. In that case, when the prevention processing is performed, the drink and food supplier may automatically supply a drink or a food to the person 200. Examples of such drinks and foods include drinks and candies that would prevent travel sickness effectively. For example, the drink and food supplier may provide a cup of herb tea that would prevent travel sickness effectively.

Examples of the prevention processing using the device system 30 include awakening memories of the past, stimulating the semicircular canals, and inducing sleep. Memories of the past may be awakened by matching the memories of the past (such as the conditions of the person 200 in the past and the atmosphere that surrounded him or her in the past) with the current conditions of the person 200 and the atmosphere currently surrounding him or her. Specifically, for that purpose, the odor control device 36 may exhale the same odor components as the ones that the person 200 smelt in the past, the same visual information (such as the vibration of the display screen of the car navigation system) as the past one may be presented again, and the temperature may be set at the same value as the past one by the air conditioner 33. Examples of stimuli to the semicircular canals include visual stimuli, olfactory stimuli, tactile stimuli, body temperature control, auditory stimuli, gustatory stimuli, and pharmaceutical benefits. The visual stimulus may be given to the person 200 by irradiating the person 200 with light for a short time. The olfactory stimulus may be given to the person 200 by exhaling intense odor components toward the person 200. The tactile stimulus may be given to the person 200 by giving subtle vibrations from the driving unit 35 to the person 200. The body temperature control of the person 200 may be made by cooling the person's 200 body with the air conditioner 33 or the cooling device 39. The auditory stimulus may be given to the person 200 by emitting a low-frequency or high-frequency sound from the loudspeaker 31. The gustatory stimulus may be given to the person 200 by providing a drink or a food that stimulates his or her taste (such as herb tea or wasabi) for him or her. The pharmaceutical benefits may be given to the person 200 by providing a relief from travel sickness that has been prepared in advance for him or her or by vaporizing the relief from travel sickness and supplying the relief to the person 200 using the air conditioner 33. Examples of sleep induction include inducing sleep with medicines, inducing sleep with vibrations, inducing sleep with music, inducing sleep by warming the cabin inside the car 100, inducing sleep by adjusting lighting inside the car 100, inducing sleep with an odor (such as the odor of aroma that produces relaxation effects), and inducing sleep with the sense of repletion. Examples of the sleep induction with music include inducing sleep with monotonous music and inducing sleep by emitting a sound as a series of hardly catchable words uttered. Note that the sleep induction with the sense of repletion may include inducing sleep indirectly by emitting a verbal message urging the person 200 to have some food.

The controller 40 needs to include at least the estimation unit 412 and the output unit 413. That is to say, the notification unit 414, the control unit 415, and the storage unit 416 are not essential constituent elements for the controller 40.

In the exemplary embodiment described above, when a plurality of persons 200 are onboard the moving vehicle (car 100), the estimation unit 412 is supposed to perform the estimation processing on each of the plurality of persons 200 on an individual basis. However, the estimation unit 412 does not have to perform the estimation processing on each of the plurality of persons 200 on an individual basis but may perform the estimation processing only on the person 200 seated on a particular seat 110.

Optionally, in performing the estimation processing, the estimation unit 412 may use a mathematical model for estimating the degree of "car sickness" (see, for example, http://www.ritsumei.ac.jp/research/radiant/robot_ai/story9.html). Nevertheless, since the estimation processing is the processing of estimating whether or not the person 200 is in circumstances that would cause travel sickness for him or her, the various types of parameters need to be adjusted in that case.

When a complexion is used as a piece of biometric information about the person 200, it is possible to estimate, by detecting a change in complexion, whether or not the person 200 is in circumstances that would cause travel sickness for him or her. A change in the person's 200 complexion is believed to be a sign of the onset of travel sickness. Therefore, it may be used as a factor in determining an estimated value about travel sickness whether the person's 200 complexion has changed or not. When the frequency of blinks is used as a piece of biometric information about the person 200, it is possible to estimate, by detecting a change in the number of times of blinks (per unit time), whether or not the person 200 is in circumstances that would cause travel sickness for him or her. It has been reported that in an initial stage of travel sickness and in case of light travel sickness, the person's facial expression turns into a so-called "empty" one. When the person's expression is empty, the number of times of blinks per unit time tends to decrease compared to his or her normal conditions. Thus, the decrease in the number of times of blinks per unit time would be a sign of the onset of travel sickness. Therefore, the change in the number of times of blinks per unit time may be used as a factor in determining the estimated value about travel sickness. The person's 200 complexion and blinks as pieces of biometric information about the person 200 may be detected using the camera 24, for example.

In the exemplary embodiment described above, the person information includes the posture information, the progress information, and the emotion information. Optionally, the person information may further include attribute information representing the person's 200 attributes. Examples of the person's 200 attributes include his or her build, age, sex, constitution, and bodily conditions. These pieces of attribute information may be entered by the person 200 him- or herself by self-certification through the car navigation system 32. These pieces of the person's 200 attribute information thus entered may be stored in the storage unit 416 of the travel sickness estimation system 10. For example, the travel sickness estimation system 10 may incorporate the person's 200 attribute information into the records of use of the car 100 by the person 200. Optionally, the attribute information entered by the person 200 into the telecommunications device 60 may be acquired by the travel sickness estimation system 10 via the communications unit 42. Furthermore, the attribute information may be presumed by the lighting turn OFF time and the air conditioner operating duration in conjunction with the electronic appliances installed in the person's 200 dwelling house or may be acquired by monitoring the infrared sensor of the air conditioner. Using the attribute information may make the specifics of the estimation processing even more suitable to the person 200. For example, the threshold value of the estimated value about travel sickness for use in the estimation processing may be adjusted according to the attribute information, thus improving the accuracy of the estimation processing. Note that the person information needs to include at least the posture information. That is to say, the progress information, the emotion information, and the attribute information are not essential constituent elements of the person information.

Optionally, the estimation unit 412 may make the storage unit 416 store the result of the estimation processing on a person 200 basis. In addition, the estimation unit 412 may accept feedback with respect to the result of the estimation processing on the person 200 basis. Such feedback may be entered through the car navigation system 32, for example. The estimation unit 412 may appropriately correct, based on the feedback, the threshold value, the reference value, and other values for use in the estimation processing on the person 200 basis. Furthermore, the estimation unit 412 may transmit information about travel sickness to the data center 50 and the telecommunications device 60 via the communications unit 42. This allows the person 200 to confirm his or her susceptibility to travel sickness and the history of travel sickness that he or she suffered in the past.

Optionally, the storage unit 416 may store the history of travel sickness on a person 200 basis. The history of travel sickness may include the history of estimation results of travel sickness by the estimation unit 412, for example. The history of travel sickness allows the travel sickness estimation system 10 to find particularly what factor tends to trigger the onset of travel sickness for the person 200 on an individual basis. For example, the estimation unit 412 may correct, based on the history of travel sickness on the person 200 basis, the threshold value, the reference value, and other values for use in the estimation processing on a person-by-person basis. For example, in the case of a person 200 that is determined to be easily susceptible to bad odors according to the history of travel sickness, the estimated value in terms of odors may be set at a relatively high value by lowering the reference value of the Factor (3) relating to odors. Meanwhile, in the case of a person 200 that is determined to have delicate semicircular canals according to the history of travel sickness, the estimated value in terms of posture may be set at a relatively high value by lowering the reference value of the Factor (1) relating to posture. This allows the estimation processing to be performed adaptively to each individual person 200, thus hopefully improving the accuracy of estimation. For example, the control unit 415 may also change, according to the history of travel sickness on the person 200 basis, the type of the prevention processing from one person 200 to another. Specifically, in the case of the person 200 that is determined to be easily susceptible to bad odors according to the history of travel sickness, the prevention processing by the odor control device 36 may be performed preferentially. Meanwhile, in the case of a person 200 that is determined to have delicate semicircular canals according to the history of travel sickness, the prevention processing by the driving unit 35 may be performed preferentially. This allows the prevention processing to be performed adaptively to each individual person 200, thus hopefully increasing the travel sickness prevention effect.

In the exemplary embodiment described above, the ratio of the high-frequency component to the low-frequency component of the heartbeat variation spectrum is used to determine whether or not the respiration frequency has increased. It is known that this ratio represents a relative stress value. In view of these considerations, the millimeter wave sensor 26 and the terahertz wave sensor 27 may be used in combination to acquire the emotion information. That is to say, this relative stress value may be used as a factor in determining the estimated value about travel sickness. Note that to obtain the heartbeat variation spectrum, at least one of the millimeter wave sensor 26 or the terahertz wave sensor 27 needs to be used and not both of the millimeter wave sensor 26 and the terahertz wave sensor 27 have to be used.

Furthermore, in the exemplary embodiment described above, the atmosphere, represented by the atmosphere information, in the internal space of the moving vehicle (car 100) is an odor. Optionally, the atmosphere may include brightness and temperature. The brightness in the internal space of the moving vehicle may be acquired by a brightness sensor. The temperature in the internal space of the moving vehicle may be acquired by a temperature sensor. The brightness and temperature could affect the person's 200 conditions. Thus, using the brightness and temperature as additional pieces of atmosphere information contributes to further improving the accuracy of the estimation processing. Nevertheless, the atmosphere information is not always required in the estimation processing.

The controller 40 may be implemented as a plurality of computers, and various functions of the controller 40 (namely, the respective functions of the input unit 411, the estimation unit 412, the output unit 413, the notification unit 414, the control unit 415, and the storage unit 416) may be distributed in a plurality of computers. For example, the notification unit 414 does not have to form part of the controller 40 but may be provided for any other one of the devices that form the notification system (such as the car navigation system 32). Alternatively, the notification unit 414 may also be distributed in a plurality of devices that form the notification system. Likewise, the control unit 415 does not have to form part of the controller 40 but may be provided for any other one of the devices that form the prevention system (such as the traveling controller 38). Alternatively, the control unit 415 may be distributed in a plurality of devices that form the prevention system. Optionally, at least part of the controller 40 may be implemented as a cloud computing system.

As can be seen, the entity that performs the functions of the travel sickness estimation system 10 includes a computer system. In that case, the computer system may include, as principal hardware components, one or more processors and one or more memories. The functions of the entity serving as the travel sickness estimation system 10 according to the present disclosure may be performed by making the one or more processors execute a program stored in the one or more memories of the computer system. The program may be stored in advance in the one or more memories of the computer system. Alternatively, the program may also be downloaded through a telecommunications line or be distributed after having been recorded in some non-transitory storage medium such as a memory card, an optical disc, or a hard disk drive, any of which is readable for the computer system. The one or more processors of the computer system may be made up of a single or a plurality of electronic circuits including a semiconductor integrated circuit (IC) or a largescale integrated circuit (LSI). Those electronic circuits may be either integrated together on a single chip or distributed on multiple chips, whichever is appropriate. Those multiple chips may be integrated together in a single device or distributed in multiple devices without limitation.

In the exemplary embodiment described above, the moving vehicle provided with the travel sickness estimation system 10 is the car 100, However, this is only an example and should not be construed as limiting. Alternatively, the travel sickness estimation system 10 may be provided for various other types of vehicles (not just the cars 10), ships or boats, and aircrafts as well. The travel sickness estimation system 10 may also be provided for a moving vehicle for use as an attraction (such as a roller coaster) in an amusement facility. Furthermore, the travel sickness estimation system 10 may also be provided for (mainly the seats of) a system that uses either a real-world screen (such as a monitor screen or a movie theater screen) or a virtual environment (such as an augmented reality (AR) or a virtual reality (VR) that uses a pair of goggles).

3. Aspects

As can be seen from the foregoing description of the exemplary embodiment and its variations, the present disclosure has the following first to twenty-second aspects. In the following description, reference signs are added in parentheses to the respective constituent elements solely for the purpose of clarifying the correspondence between those aspects of the present disclosure and the exemplary embodiment described above.

A travel sickness estimation system (10) according to a first aspect includes an estimation unit (412) and an output unit (413). The estimation unit (412) is configured to perform estimation processing of estimating, based on person information indicating conditions of a person (200) who is on board a moving vehicle (100), whether or not the person (200) is in circumstances that would cause travel sickness for him or her. The output unit (413) is configured to output a result of the estimation processing performed by the estimation unit (412). The first aspect can reduce the onset of travel sickness.

A travel sickness estimation system (10) according to a second aspect may be implemented in combination with the first aspect. In the second aspect, the estimation unit (412) is configured to perform the estimation processing with reference to not only the person information but also vehicle information indicating conditions of the moving vehicle (100). The second aspect can improve the accuracy of the estimation processing.

A travel sickness estimation system (10) according to a third aspect may be implemented in combination with the second aspect. In the third aspect, the vehicle information includes at least one of behavior information indicating a behavior of the moving vehicle (100) and atmosphere information indicating an atmosphere in an internal space of the moving vehicle (100). The third aspect can improve the accuracy of the estimation processing.

A travel sickness estimation system (10) according to a fourth aspect may be implemented in combination with any one of the first to third aspects. In the fourth aspect, the person information includes at least one of: posture information indicating the person's (200) posture; attribute information indicating the person's (200) attributes; progress information indicating how the person's (200) biometric information has changed; or emotion information indicating the person's (200) emotions. The fourth aspect can improve the accuracy of the estimation processing.

A travel sickness estimation system (10) according to a fifth aspect may be implemented in combination with the fourth aspect. In the fifth aspect, the person information includes the posture information. The estimation unit (412) is connected to, and is able to communicate with, a pressure sensor (23) configured to detect at least one of a center of gravity of the person (200) or a distribution of pressures applied by the person (200) to the moving vehicle (100). The estimation unit (412) is configured to determine, based on an output of the pressure sensor (23), the person's (200) posture. The fifth aspect can improve the accuracy of the estimation processing.

A travel sickness estimation system (10) according to a sixth aspect may be implemented in combination with any one of the first to fifth aspects. In the sixth aspect, the travel sickness estimation system (10) includes a notification system (414, 31, 32) configured to receive the result of the estimation processing from the output unit (413). The notification system (414, 31, 32) is configured to, when the result of the estimation processing indicates that the person (200) is in the circumstances that would cause travel sickness for him or her, perform notification processing of notifying the person (200) of the chances of having travel sickness. The sixth aspect can contribute to preventing the onset of travel sickness.

A travel sickness estimation system (10) according to a seventh aspect may be implemented in combination with any one of the first to sixth aspects. In the seventh aspect, the travel sickness estimation system (10) includes a prevention system (415, 32-39) configured to receive the result of the estimation processing from the output unit (413). The prevention system (415, 32-39) is configured to, when the result of the estimation processing indicates that the person (200) is in the circumstances that would cause travel sickness for him or her, perform prevention processing of preventing the person (200) from suffering travel sickness. The seventh aspect can contribute to preventing the onset of travel sickness.

A travel sickness estimation system (10) according to an eighth aspect may be implemented in combination with any one of the first to fifth aspects. In the eighth aspect, the travel sickness estimation system (10) includes: a notification system (414, 31, 32) configured to receive the result of the estimation processing from the output unit (413); and a prevention system (415, 32-39) configured to receive the result of the estimation processing from the output unit (413). The notification system (414, 31, 32) is configured to, when the result of the estimation processing indicates that the person (200) is in the circumstances that would cause travel sickness for him or her, perform notification processing of notifying the person (200) of the chances of having travel sickness. The prevention system (415, 32-39) is configured to perform prevention processing of preventing the person (200) from suffering travel sickness when the result of the estimation processing still indicates, even after the notification system (414, 31, 32) has performed the notification processing, that the person (200) is in the circumstances that would cause travel sickness for him or her. The eighth aspect can contribute to preventing the onset of travel sickness.

A travel sickness estimation system (10) according to a ninth aspect may be implemented in combination with the seventh or eighth aspect. In the ninth aspect, the prevention system (415, 32-39) includes a driving unit (35) installed in a seat (110) of the moving vehicle (100) and configured to change a surface shape of the seat (110). The ninth aspect can contribute to preventing the onset of travel sickness due to the posture of the person (200).

A travel sickness estimation system (10) according to a tenth aspect may be implemented in combination with the ninth aspect. In the tenth aspect, the driving unit (35) includes one or more actuators (351, 352, 353) installed in at least one of a bearing surface (111) of the seat (110) or a backrest (112) of the seat (110). The tenth aspect can contribute to preventing the onset of travel sickness due to the posture of the person (200).

A travel sickness estimation system (10) according to an eleventh aspect may be implemented in combination with any one of the seventh to tenth aspects. In the eleventh aspect, the prevention system (415, 32-39) includes an odor control device (36) having a component for controlling an odor inside the moving vehicle (100). The eleventh aspect can contribute to preventing the onset of travel sickness due to an odor in the moving vehicle (100).

A travel sickness estimation system (10) according to a twelfth aspect may be implemented in combination with any one of the seventh to eleventh aspects. In the twelfth aspect, the prevention system (415, 32-39) includes a relaxation device (37) configured to produce a relaxation effect on the person (200). The twelfth aspect can contribute to preventing the onset of travel sickness.

A travel sickness estimation system (10) according to a thirteenth aspect may be implemented in combination with any one of the seventh to twelfth aspects. In the thirteenth aspect, the prevention system (415, 32-39) includes a traveling controller (38) configured to control the moving vehicle's (100) traveling. The thirteenth aspect can contribute to preventing the onset of travel sickness.

A travel sickness estimation system (10) according to a fourteenth aspect may be implemented in combination with the thirteenth aspect. In the fourteenth aspect, the traveling controller (38) is configured to control, in the prevention processing, the moving vehicle's (100) traveling to relieve a burden on the person (200). The fourteenth aspect can contribute to preventing the onset of travel sickness.

A travel sickness estimation system (10) according to a fifteenth aspect may be implemented in combination with the thirteenth or fourteenth aspect. In the fifteenth aspect, the traveling controller (38) is configured to change, in the prevention processing, specifics of control of the moving vehicle (100) according to a remaining traveling time that it takes for the moving vehicle (100) to arrive at its destination. The fifteenth aspect can contribute to preventing the onset of travel sickness.

A travel sickness estimation system (10) according to a sixteenth aspect may be implemented in combination with any one of the seventh to fifteenth aspects. In the sixteenth aspect, the prevention system (415, 32-39) includes a cooling device (39) configured to cool a part of the person's (200) body. The sixteenth aspect can contribute to preventing the onset of travel sickness.

A travel sickness estimation system (10) according to a seventeenth aspect may be implemented in combination with any one of the first to sixteenth aspects. In the seventeenth aspect, the travel sickness estimation system (10) further includes a communications unit (42) configured to communicate with a data center (50) that collects information about travel sickness. The seventeenth aspect can improve the accuracy of the estimation processing.

A travel sickness estimation system (10) according to an eighteenth aspect may be implemented in combination with the seventeenth aspect. In the eighteenth aspect, the travel sickness estimation system (10) includes a storage unit (416) configured to store an estimation algorithm for determining specifics of the estimation processing. The estimation unit (412) is configured to correct, based on information provided by the data center (50), the estimation algorithm stored in the storage unit (416). The eighteenth aspect can improve the accuracy of the estimation processing.

A travel sickness estimation system (10) according to a nineteenth aspect may be implemented in combination with any one of the first to eighteenth aspects. In the nineteenth aspect, the estimation unit (412) is configured to, when a plurality of persons (200) are on hoard the moving vehicle (100), perform the estimation processing on each of the plurality of persons (200) on an individual basis. The nineteenth aspect can reduce the onset of travel sickness for a plurality of persons (200) who are on board the same moving vehicle (100).

A moving vehicle (100) according to a twentieth aspect includes: the travel sickness estimation system (10) according to any one of the first to nineteenth aspects; and a body (101) on which the travel sickness estimation system (10) is installed. The twentieth aspect can reduce the onset of travel sickness.

A travel sickness estimation method according to a twenty-first aspect includes a first step and a second step. The first step includes performing estimation processing of estimating, based on person information indicating conditions of a person (200) who is on board a moving vehicle (100), whether or not the person (200) is in circumstances that would cause travel sickness for him or her. The second step includes outputting a result of the estimation processing. The twenty-first aspect can reduce the onset of travel sickness.

A travel sickness estimation program according to a twenty-second aspect is designed, when executed by one or more processors, to give a first instruction and a second instruction to the one or more processors. The first instruction is an instruction to perform estimation processing of estimating, based on person information indicating conditions of a person (200) who is on board a moving vehicle (100), whether or not the person (200) is in circumstances that would cause travel sickness for him or her. The second instruction is an instruction to output a result of the estimation processing. The twenty-second aspect can reduce the onset of travel sickness.

REFERENCE SIGNS LIST

10 Travel Sickness Estimation System
21a Acceleration Sensor
21b Angular Velocity Sensor
22 Odor Sensor
23 Pressure Sensor
24 Camera
25 Infrared Sensor
26 Millimeter Wave Sensor
27 Terahertz Wave Sensor
28 Breath Sensor
29 Sensor Unit
31 Loudspeaker
32 Car Navigation System
33 Air Conditioner
34 Power Window
35 Driving Unit
351 First Actuator
352 Second Actuator
353 Third Actuator
36 Odor Control Device
37 Relaxation Device
38 Traveling Controller
39 Cooling Device
412 Estimation unit
413 Output Unit
414 Notification Unit
415 Control Unit
416 Storage Unit
42 Communications Unit
50 Data Center
100 Car (Moving Vehicle)
110 Seat
111 Bearing Surface
112 Backrest
200 Person

The invention claimed is:

1. A travel sickness estimation system comprising:
 a controller including:
  an estimation unit configured to perform estimation processing of estimating, based on person information indicating conditions of a person who is on board a moving vehicle, whether or not the person is in circumstances that would cause travel sickness for the person; and
  an output unit configured to output a result of the estimation processing performed by the estimation unit; and
 a prevention system configured to receive the result of the estimation processing from the output unit, wherein:
 the controller is implemented as a combination of one or more processors and one or more memories,
 the estimation unit is configured to perform the estimation processing with reference to not only the person information but also vehicle information indicating conditions of the moving vehicle,
 the person information includes posture information indicating the person's posture,
 the person's posture is represented by a tilt angle defined by a center axis of the person's head with respect to a center axis of the person's body trunk and a tilt angle defined by the center axis of the person's body trunk with respect to a horizontal plane,
 the vehicle information includes behavior information indicating a behavior of the moving vehicle,
 the prevention system is configured to, when the result of the estimation processing indicates that the person is in the circumstances that would cause travel sickness for the person, perform prevention processing of preventing the person from suffering travel sickness,
 the prevention system includes a driving unit installed in a seat of the moving vehicle and configured to change a surface shape of the seat, and
 the estimation unit is configured, in the estimation processing, to
  when finding a tilt angle or the moving vehicle's traveling direction or propulsion greater than a corresponding reference value, respectively, obtain magnitude of a gap between the behavior of the moving vehicle and the person's posture to increase an estimated value about travel sickness according to the magnitude of the gap, and
  when the magnitudes of the gap between the behavior of the moving vehicle and the person's posture are accumulated to make the estimated value equal to or greater than a threshold value, make a determination that the person is in circumstances that would cause travel sickness for the person.

2. The travel sickness estimation system of claim 1, wherein
the vehicle information includes atmosphere information indicating an atmosphere in an internal space of the moving vehicle.

3. The travel sickness estimation system of claim 1, wherein
the person information includes at least one of:
attribute information indicating the person's attributes;
progress information indicating how the person's biometric information has changed; or
emotion information indicating the person's emotions.

4. The travel sickness estimation system of claim 3, wherein
the estimation unit is connected to, and is able to communicate with, a pressure sensor configured to detect at least one of a center of gravity of the person or a distribution of pressures applied by the person to the moving vehicle, and
the estimation unit is configured to determine, based on an output of the pressure sensor, the person's posture.

5. The travel sickness estimation system of claim 1, comprising a notification system configured to receive the result of the estimation processing from the output unit, wherein
the notification system is configured to, when the result of the estimation processing indicates that the person is in the circumstances that would cause travel sickness for the person, perform notification processing of notifying the person of the chances of having travel sickness.

6. The travel sickness estimation system of claim 1, comprising:
a notification system configured to receive the result of the estimation processing from the output unit, wherein
the notification system is configured to, when the result of the estimation processing indicates that the person is in the circumstances that would cause travel sickness for the person, perform notification processing of notifying the person of the chances of having travel sickness, and
the prevention system is configured to perform the prevention processing when the result of the estimation processing still indicates, even after the notification system has performed the notification processing, that the person is in the circumstances that would cause travel sickness for the person.

7. The travel sickness estimation system of claim 1, wherein
the driving unit includes one or more actuators installed in at least one of a bearing surface of the seat or a backrest of the seat.

8. The travel sickness estimation system of claim 1, wherein
the prevention system includes an odor control device having a component for controlling an odor inside the moving vehicle.

9. The travel sickness estimation system of claim 1, wherein
the prevention system includes a traveling controller configured to control the moving vehicle's traveling.

10. The travel sickness estimation system of claim 9, wherein
the traveling controller is configured to control, in the prevention processing, the moving vehicle's traveling to relieve a burden on the person.

11. The travel sickness estimation system of claim 9, wherein
the traveling controller is configured to change, in the prevention processing, specifics of control of the moving vehicle according to a remaining traveling time for the moving vehicle to arrive at its destination.

12. The travel sickness estimation system of claim 1, wherein
the prevention system includes a cooling device configured to cool a part of the person's body.

13. The travel sickness estimation system of claim 1, further comprising a communications unit configured to communicate with a data center that collects information about travel sickness.

14. The travel sickness estimation system of claim 13, comprising a storage unit configured to store an estimation algorithm for determining specifics of the estimation processing, wherein
the estimation unit is configured to correct, based on information provided by the data center, the estimation algorithm stored in the storage unit.

15. The travel sickness estimation system of claim 1, wherein
the estimation unit is configured to, when a plurality of persons are on board the moving vehicle, perform the estimation processing on each of the plurality of persons on an individual basis.

16. The travel sickness estimation system of claim 1, wherein
the prevention system controls the driving unit to change the surface shape of the seat according to at least one of acceleration or angular velocity of the moving vehicle to relieve burden on the person.

17. A moving vehicle comprising:
a travel sickness estimation system; and
a body on which the travel sickness estimation system is installed, wherein:
the travel sickness estimation system comprises:
a controller including
an estimation unit configured to perform estimation processing of estimating, based on person information indicating conditions of a person who is on board a moving vehicle, whether or not the person is in circumstances that would cause travel sickness for the person; and
an output unit configured to output a result of the estimation processing performed by the estimation unit and
a prevention system configured to receive the result of the estimation processing from the output unit,
the controller is implemented as a combination of one or more processors and one or more memories,
the estimation unit is configured to perform the estimation processing with reference to not only the person information but also vehicle information indicating conditions of the moving vehicle,
the person information includes posture information indicating the person's posture,
the person's posture is represented by a tilt angle defined by a center axis of the person's head with respect to a center axis of the person's body trunk and a tilt angle defined by the center axis of the person's body trunk with respect to a horizontal plane,
the vehicle information includes behavior information indicating a behavior of the moving vehicle,
the prevention system is configured to, when the result of the estimation processing indicates that the person is in the circumstances that would cause travel sickness for the person, perform prevention processing of preventing the person from suffering travel sickness, the prevention system includes a driving unit installed in a seat of the moving vehicle and configured to change a surface shape of the seat, the estimation unit is configured, in the estimation processing, to when finding a tilt angle or the moving vehicle's traveling direction or propulsion greater than a corresponding reference value, respectively, obtain magnitude of a gap between the behavior of the moving vehicle and the person's posture to increase an estimated value about travel sickness according to the magnitude of the gap, and when the magnitudes of the gap between the behavior of the moving vehicle and the person's posture are accumulated to make the estimated value equal to or greater than a threshold value, make a determination that the person is in circumstances that would cause travel sickness for the person.

18. A travel sickness estimation method comprising:

performing estimation processing of estimating, based on person information indicating conditions of a person who is on board a moving vehicle, whether or not the person is in circumstances that would cause travel sickness for the person; and when a result of the estimation processing indicates that the person is in the circumstances that would cause travel sickness for the person, performing, by a prevention system, prevention processing of preventing the person from suffering travel sickness, wherein:

the estimation processing references to not only the person information but also vehicle information indicating conditions of the moving vehicle, the person information includes posture information indicating the person's posture, the person's posture is represented by a tilt angle defined by a center axis of the person's head with respect to a center axis of the person's body trunk and a tilt angle defined by the center axis of the person's body trunk with respect to a horizontal plane, the vehicle information includes behavior information indicating a behavior of the moving vehicle, the estimation processing estimates, when finding a tilt angle or the moving vehicle's traveling direction or propulsion greater than a corresponding reference value, respectively, obtain magnitude of a gap between the behavior of the moving vehicle and the person's posture to increase an estimated value about travel sickness according to the magnitude of the gap, and when the magnitudes of the gap between the behavior of the moving vehicle and the person's posture are accumulated to make the estimated value equal to or greater than a threshold value, make a determination that the person is in circumstances that would cause travel sickness for the person, and the prevention system includes a driving unit installed in a seat of the moving vehicle and configured to change a surface shape of the seat.

\* \* \* \* \*